United States Patent [19]

Labeeuw et al.

[11] Patent Number: 4,604,387
[45] Date of Patent: Aug. 5, 1986

[54] 1,2,4-TRIAZINYLTHIOMETHYL-3-CEPHEM SULFOXIDES, AND A PROCEDURE FOR THEIR PREPARATION

[75] Inventors: Bernard Labeeuw, Montpellier; Ali Sahli, St Gely du Fesc, both of France

[73] Assignee: Sanofi, Paris, France

[21] Appl. No.: 525,797

[22] Filed: Aug. 23, 1983

Related U.S. Application Data

[63] Continuation of Ser. No. 277,839, Jun. 26, 1981, abandoned.

[30] Foreign Application Priority Data

Jun. 30, 1980 [FR] France ............... 80 14512
Mar. 3, 1981 [FR] France ............... 81 04242
Mar. 3, 1981 [FR] France ............... 81 04243

[51] Int. Cl.$^4$ ............... A61K 31/545; C07D 501/60
[52] U.S. Cl. ............... 514/206; 540/227
[58] Field of Search ............... 544/27; 424/246

[56] References Cited

U.S. PATENT DOCUMENTS 4,399,131 8/1983 Durckheimer et al. ............ 544/28

Primary Examiner—Robert Gerstl
Assistant Examiner—Mary E. Ceperley
Attorney, Agent, or Firm—Weingarten, Schurgin, Gagnebin & Hayes

[57] ABSTRACT

Cephalosporin derivatives effective against gram-negative bacteria and virtually inactive against staphylococci are disclosed. The derivatives have the following general formula:

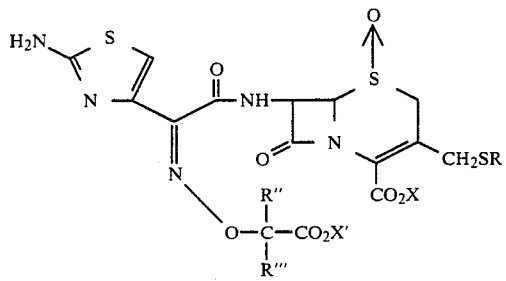

in which
R is

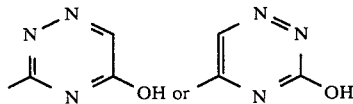

R″ and R‴ are hydrogen, lower alkyl or together are 1,3-propylene or 1,4-butylene, and X and X′ are hydrogen, cation or easily metabolically labile and pharmaceutically acceptable ester or hemiacetal.

4 Claims, No Drawings

1,2,4-TRIAZINYLTHIOMETHYL-3-CEPHEM SULFOXIDES, AND A PROCEDURE FOR THEIR PREPARATION

This application is a continuation of application Ser. No. 277,839, filed June 26, 1981, now abandoned.

This present invention relates to a series of new cephalosporin sulfoxides, a procedure for their preparation, and pharmaceutical compositions containing a cephalosporin sulfoxide as active substance. In particular, this present invention relates to new cephalosporin sulfoxides having a 1,2,4-triazinylthiomethyl group at position 3 of the cephem ring.

Belgian Pat. No. 866038 describes a series of cephalosporin sulfoxides and sulphones having the general formula:

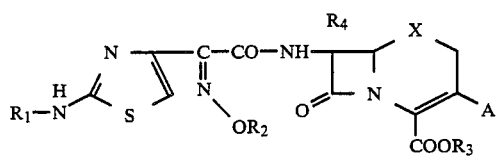

The above-cited patent defines A to include the $CH_2SR_5$ group, where $R_5$ can be triazinyl, in particular 1,3,4-triazin-2-yl and 1,3,5-triazin-1-yl which may be substituted. More particularly, it covers compounds with formula (I) where:

in one instance $R_1=H$; $R_2=H$; $R_3=H$; $R_4=H$; $X=SO$

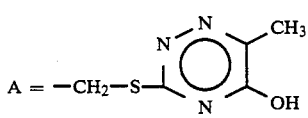

and in another instance $R_1=H$; $R_2$ is $CH_2-CH=CH_2$;

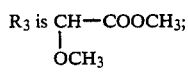

$R_4=H$; $X=SO$

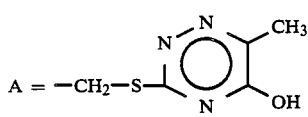

without, however, describing them specifically.

Cephalosporins of formula (I) listed above are generally expected to show a high degree of anti-bacterial activity against both gram-positive and gram-negative bacteria, being highly efficient against penicilinase-positive staphylococcus with a certain degree of fungistatic activity.

We have found that certain 1-oxide cephalosporins having a 1,2,4-triazin-3-yl group at position 3 on the cephem ring substituted in position 5 with a hydroxyl or a 1,2,4-triazin-5-yl group substituted in position 3 with a hydroxyl show a completely different anti-bacterial profile from that of the compounds described in Belgian Pat. No. 866038. Surprisingly it was found that the 1-oxide cephalosporins are remarkably effective against gram-negative bacteria, including beta-lactamase producing strains, and in particular, enterobacteria: on the other hand, they are virtually inactive against staphylococci, whether beta-lactamase positive or not.

Thus, the present invention relates to 3-(hydroxyl-1,2,4-triazinyl)thiomethyl cephalosporins with the formulae:

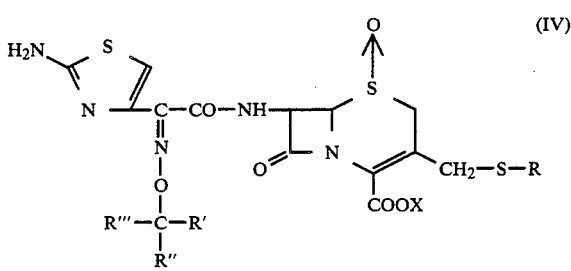

in which:
R is:

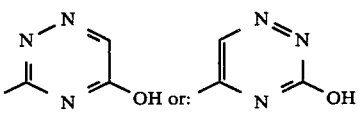

R' is hydrogen or a COOX' carboxyl group

R" and R''' which can be identical or different from each other, each represent hydrogen or a lower alkyl group or, together, a 1,3-propylene or 1,4-butylene radical.

X and X' which can be identical or different represent hydrogen, a cation, an ester or an easily hydrolizable or metabolically labile and pharmaceutically acceptable hemiacetal.

The term "lower alkyl", as used here, designates the radical of a saturated hydrocarbon containing up to 3 carbon atoms, i.e. methyl, ethyl, propyl, isopropyl.

The term "cation" here designates an alkaline or alkaline earth-metal ion, preferably sodium, potassium or calcium, or a proton linked to a pharmaceutically acceptable organic amine such as ethylenediamine, triethanolamine, diethanolamine, ethanolamine, tromethamine or other such charged species capable of forming salts.

The term "ester or metabolically labile or easily hydrolizable and pharmaceutically acceptable hemiacetal" designates radicals which are generally used to form drugs with pharmacologically active carboxylic acids, preferably the following radicals: phthalidyl, pivaloyloxymethyl, acetoxymethyl, ethoxycarbonyloxymethyl, 1-(ethoxycarbonyloxy)ethyl, acetonyl, alpha-methoxy alpha-carbomethoxymethyl, carbomethoxymethyl, carbethoxymethyl, etc.

Due to the presence of an oxime group, the compounds (IV) exist in two different isomeric forms. The cis-isomers, the therapeutic activity of which is greater, are the preferred form. It is understood that compounds (IV) indicated here-above can exist:
either in the form indicated in formula (IV),
or as a tautomer IV':

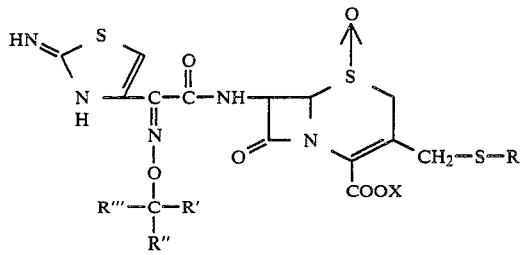

in which R, R', R", R''' and X are defined as above.

The invention also relates to procedures for the preparation of compounds of formula (IV).

A first procedure has the following steps:

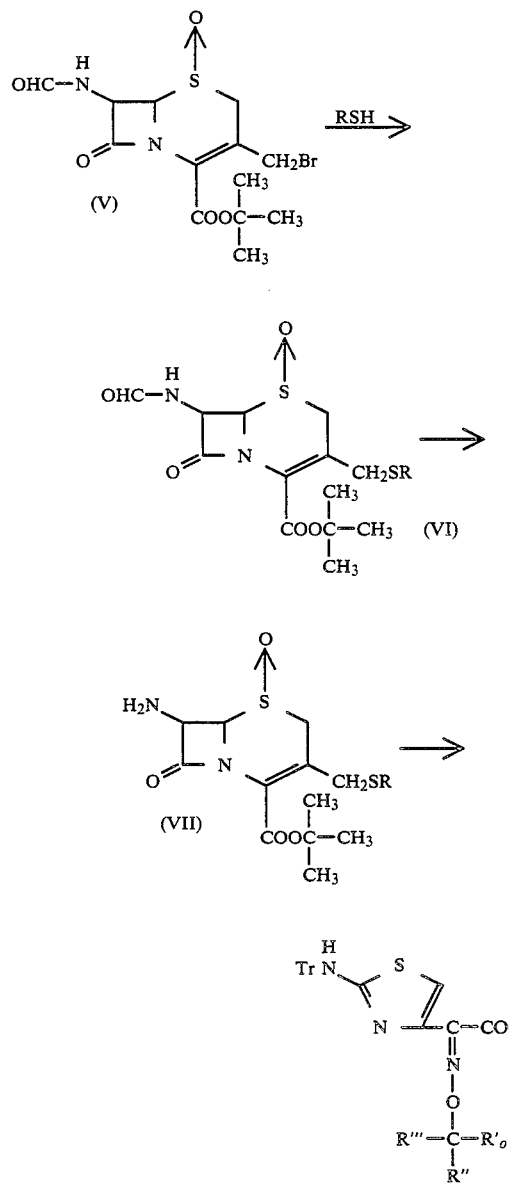

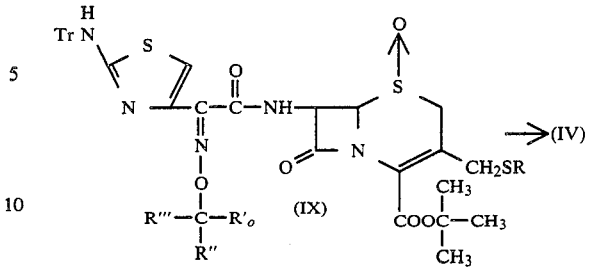

Tr = trytyl

The starting compound is a sulfoxide (V) which is reacted with a compound R—SH in dimethylformamide solution in the presence of a base such as triethylamine to yield a compound substituted at position 3 (VI). The amino group is liberated by the action of thionyl chloride in solution, and compound (VII) is isolated as the hydrochloride. This is acylated with a compound of formula (VIII) in which R" and R''' are as defined above and $R'_o$ represents hydrogen or $COOX'_o$ or $X'_o$ represents an easily hydrolizable hemiacetal or ester group, preferably t-butyl.

Before carrying out the acylation reaction, it is desirable to substitute the amino group of the acid with a protective group which can be easily eliminated subsequently. The groups usually used in organic synthesis for protecting amines can be used, in particular the trityl radical.

To carry out the acylation reaction, it is necessary to activate the carboxyl group of the compound (VIII), preferably by transformation to an anhydride using a carbodiimide, generally dicyclohexylcarbodiimide.

The activation reaction is carried out in an organic solvent such as tetrahydrofuran at a temperature ranging between 0° and 50° C., preferably at room temperature. The activation reaction can be facilitated by addition of a hydroxyl derivative such as 1-hydroxy benzotriazole.

The acylation reagent solution obtained, which is filtered to remove dicyclohexylurea, is added to a solution of compound (VII) in a solvent such as dimethylformamide. The order of addition of the 2 reagents can be reversed.

After the acylation reaction, the group protecting the amine, the t-butyl ester and the X' group are eliminated by a known procedure, in particular acid hydrolysis using organic acids such as formic acid or trifluoroacetic acid.

The compounds (V) and compound (VIII) as well as their derivatives in which the amine group is blocked by a protector group, are already known.

A variant of the procedure consists in the initial acylation of 7-amino 3-bromomethyl 3-cephem 4-t-butyl carboxylate (X) with an acid (VIII). Subsequent steps are those described for acylation of compounds (VII).

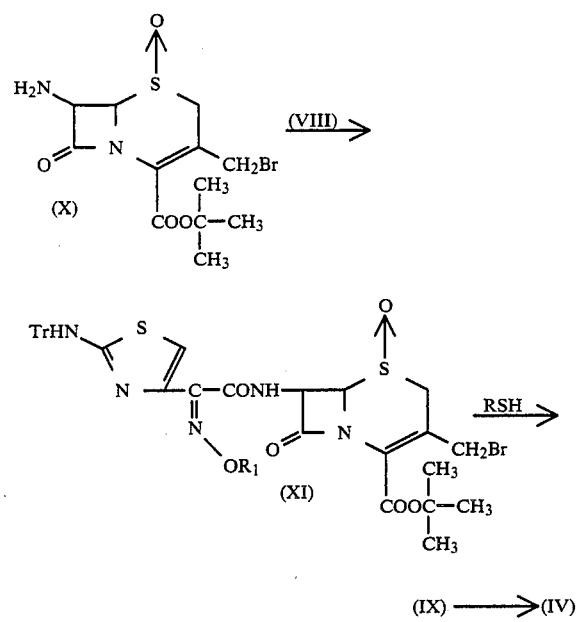

By reaction of the thiol R—SH with the compound (XI) thus obtained, the corresponding compound (IX) is produced. Conditions are the same as those indicated for production of compounds (VI).

As previously indicated, the compounds (IX) treated with a strong acid give compounds (IV). A second procedure for the preparation of compounds (VI) from the corresponding non-sulfoxide derivatives comprises reacting them with an organic peracid such as 3-chloro perbenzoic acid.

The reaction is carried out in solution and at a temperature between 10° and 30° C.

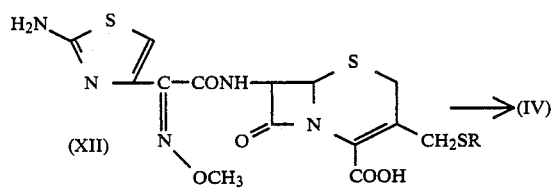

Of the compounds (XII), some are already known, and others have been described in the French application filed by the applicant on Mar. 26th, 1980, number 80/06757.

Compound (IV) in which X is other than H may be produced from compounds (IV) in which X is H by reactions which are already well-known.

Mineral salts are obtained by reaction with mineral bases such as sodium or potassium hydroxide, sodium bicarbonate in equimolar quantities of compounds (IV) in which X is equivalent to H. The salification reaction is carried out in a solvent such as water or ethanol, and the salt obtained isolated by evaporation of the solution.

Salts of organic bases are produced by the action of an equimolar quantity of an organic base on a solution of the acid (IV, X=H) in an appropriate solvent or solvent mixture. The salt is isolated by ether precipitation.

Salts of the compounds of (IV) can also be obtained in which R'=COOX' and X' is H, as well as preferably, salts obtained by salification of compounds (IV) in which X is H and R' is COOX' and X' is H.

Hemiacetals and esters are obtained by currently known esterification procedures; by way of example, a halogenated derivative can act upon a salt such as the sodium salt of the acid. The reaction will be best realized in a solvent capable of dissolving the starting acid derivative, e.g. dimethylformamide.

It is also possible to prepare derivatives of compounds with formula (IV) where X or X' or both are other than hydrogen.

Syn isomerism is determined by reagent choice. The compounds described in this patent application possess a high degree of activity against gram-negative bacteria, notably against strains producing beta-lactamases.

In particular, compounds of formula (IV) are highly active, both against pseudomonas and against enterobacteria, this being unusual for cephalosporins. They are also active against certain strains of proteus, serratia and klebisella.

Substances described in this application also have a particularly long duration of action; by way of example, 7-[2-(2-amino 4-thiazolyl)-2-(2-carboxy-2-propyloxyimino)acetamido]-3-[(5-hydroxy-1,2,4-triazin-3-yl)thiomethyl]-3-cephem-4-carboxylic acid 1-S-oxide, syn-isomer designated by code number CM 40766 has a half life of more than 4 hours.

These compounds show a very low toxicity.

The present application also includes pharmaceutical compositions with, as active ingredient, compounds of formula (IV) described above.

Pharmaceutical compositions containing the compounds of this invention can be formulated for oral, sublingual, subcutaneous, intramuscular, intravenous, intradermal or rectal administration, combining the active drug substances with the classical pharmaceutical vehicles. Administration can be in the form of unit doses for animals or humans for the treatment of infection, in particular those due to gram-negative organisms including those which produce beta-lactamases.

In order to obtain the anti-bacterial effect required, the dose of the active drug substance can range between 10 and 500 mg per kg of body weight per day.

Each unit dose can contain 10 to 10,000 mg active drug substance in combination with the pharmaceutical excipients. This unit dose can be administered 1 to 4 times daily. Possible dose forms include tablets, capsules, powders, granulates and oral suspensions, tablets for sublingual administration, supositories and ampules for parenteral administration.

When a solid composition is prepared in the form of tablets, the active drug substance is mixed with a pharmaceutical vehicle such as gelatin, starch, lactose, magnesium stearate, talc, gum arabic, etc. Tablets can be coated with sucrose or other appropriate materials, or can be treated so that the release will be prolonged or retarded, with continuous release of a predetermined quantity of the active principle.

Capsules can be prepared by mixing the active drug substance with a vehicle and packing this mixture into hard or soft capsules.

Syrups or elixirs can contain the active drug substance along with a low-calorie sweetening agent, methylparaben and propylparaben as antiseptics, as well as appropriate flavoring and coloring agents.

Powders or water-dispersible granules can contain the active ingredient mixed with dispersing or wetting agents, suspending agents such as polyvinylpyrrolidone and with coloring and flavoring agents.

For oral administration as drops, or for parenteral administration, aqueous solutions, isotonic saline solutions, or sterile injectable solutions containing dispersing agents and/or pharmacologically compatible wetting agents are used, for example propyleneglycol or butyleneglycol.

The active principle can also be formulated in the form of microcapsules, possibly containing various structural supports or additives.

The following examples give a clearer understanding of the scope of the invention.

As is usual in this family of compounds, these products do not have a clear melting point, but rather show decomposition points which do not allow characterization. They will thus be characterized by their nuclear magnetic resonance spectra recorded at 60M Hz, the internal standard being hexamethylenedisiloxane.

The following abbreviations will be used:
S: singlet
D: doublet
D-D: doublet-doublet
e.S.: enlarged singlet
M: multiplet
AB: AB system
J: represents the coupling constant.

In all cases, elemental microanalysis confirms the formulas listed.

EXAMPLE 1

7-[2-(2-amino-4-thiazolyl)-2-methoxyimino acetamido]-3-[(3-hydroxy-1,2,4-triazin-5-yl)thiomethyl]-3-cephem-4-carboxylic acid, 1-S-oxide, cis isomer (CM 40 583)

(a)

7-[2-(2-tritylamino-4-thiazolyl)-2-methoxyiminoacetamido]-3-bromoethyl-3-cephem-4-t-butylcarboxylate 1-S-oxide, syn isomer To a solution 3.26 g 7-amino-3-bromomethyl-3-cephem-4-t-butylcarboxylate 1-S-oxide hydrochloride in 58 ml anhydrous methylene chloride, add 1.12 ml triethylamine, 3.94 g 2-(2-tritylamino-4-thiazolyl)-2-(t-butoxycarbonylmethoxyimino)-acetic acid, cis isomer, 1.84 g dicyclohexyl-carbodiimide and 0.1 g 1-hydroxy benzotriazole.

Agitate at room temperature for 3.5 hours, then filter off the dicyclohexylurea formed. Vacuum concentrate the solvent to approximately 10 ml, then carry out silica gel chromatography.

Elution with hexane/ethyl acetate 60/40 (vol/vol) yields the expected product (2.4 g).

NMR Spectrum 1H at 8.82 ppm (N$\underline{H}$—CO, D, J=8 Hz); 1H at 8.70 ppm (N$\underline{H}$-trityl, S); 15$\underline{H}$ at 7.32 ppm (Aromatic H, S); 1 at 6.78 ppm (H thiazole, S); 1H at 5.79 ppm (H$_7$, D-D, J$_1$=8 Hz, J$_2$=4.5 Hz); 1H at 4.96 ppm (H$_6$, D, J=4.5 Hz); 2H at 4.50 ppm (C$\underline{H_2}$ Br, e.S); 3H at 3.78 ppm (C$\underline{H_3}$O—, S); 2H at 3.77 ppm (C$\underline{H_2}$S→O, e.S.); 9H at 1.46 ppm

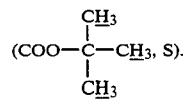

(b)

7-[2-(2-tritylamino-4-thiazolyl)-2-methoxyiminoacetamido]-3-[(3-hydroxy-1,2,4-triazin-5-yl)thiomethyl]-3-cephem-4-t-butylcarboxylate 1-S-oxide, syn isomer Agitate a 0.8 g solution of the brominated derivative produced in Example 1a for 2 hours at room temperature along with 0.16 g 3-hydroxy 5-mercapto 1,2,4-triazine in dimethylformamide.

Vacuum evaporate the solvent and dissolve the residue in isopropyl ether. Free the precipitate of solvent by vacuum filtration and redissolve in the minimum necessary quantity of methylene chloride. Carry out chromatography on a silica gel column (50 g).

By eluting with ethyl acetate, 0.50 g of the expected product were obtained.

(c) CM 40 583

Allow 0.310 g of the product obtained in step b to stand for 30 minutes at room temperature in 3.1 ml trifluoroacetic acid. Concentrate to 2 ml under vacuum and precipitate the product by addition of isopropyl ether. The solid is isolated by vacuum filtration and is vacuum dried.

The solid is purified by agitation in 60 ml 90° ethanol, yielding 0.100 g CM 40 583. Treatment of the solution with activated charcoal and concentration to a small volume yields a further 0.030 g of the expected product.

NMR Spectrum 1H at 8.95 ppm (N$\underline{H}$—CO—, D, J=8.5 Hz); 1H at 7.98 ppm (H triazine, $\overline{S}$); 4H at 7.00 ppm (O$\underline{H}$, COO$\underline{H}$, N$\underline{H_2}$, e.S.); 1H at 6.89 ppm (H thiazole, S); 1H at 5.$\overline{88}$ ppm (H$_7$, D-D, J$_1$=9 Hz, J$_2$=4 Hz); 1H at 4.96 ppm (H$_6$, D, J=4 Hz); 1H at 4.42 ppm (C$\underline{H}$S, A of AB, J=13 Hz); 1H at 4.05 ppm (C$\underline{H}$S, B of A$\overline{B}$; J=13 Hz); 3.85 ppm (C$\underline{H_3}$; and C$\underline{H_2}$S→O, M).

EXAMPLE 2

7-[2-(2-amino-4-thiazolyl)-2-carboxymethoxyiminoacetamido]-3-[(3-hydroxy-1,2,4-triazin-5-yl)thiomethyl]-3-cephem-4-carboxylic acid 1-S-oxide, syn isomer. (CM 40 515)

(a)

7-[2-(2-tritylamino-4-thiazolyl)-2-t-butoxycarboxylmethoxyiminoacetamido]-3-bromomethyl-3-cephem-4-t-butylcarboxylate 1-S-oxide To a solution of 3.26 g 7-amino-3-bromomethyl-3-cephem-4-t-butylcarboxylate 1-S-oxide hydrochloride in 58 ml anhydrous methylene chloride, add 1.12 ml of ethylamine 4.86 g 2-(2-tritylamino-4-thiazolyl)-2-(t-butoxycarbonylmethoxyimino)-acetic acid, cis isomer, 1.84 g dicyclohexyl-carbodiimide 0.1 g 1-hydroxy benzotriazole.

Agitate at room temperature for 3.5 hours, then filter off the dicyclohexylurea formed. Vacuum concentrate the solvent until approximately 10 ml, then carry out column chromatography on silica gel.

Elution with hexane/ethyl acetate 60/40 (vol/vol) yields the expected product (2.8 g).

NMR Spectrum 1H at 8.75 ppm (NH-Trit, S); 1H at 8.57 ppm (NH—CO, D, J=8.5 Hz); 15H at 7.28 ppm (Aromatic H, S); 1H at 6.82 ppm (H thiazole, S); 1H at 5.84 ppm (H$_7$, D-D, J$_1$=8.5 Hz, J$_2$=4.5 Hz); 1H at 4.98 ppm (H$_6$, D, J=4.5 Hz); 4H at 4.50 ppm (CH$_2$Br and OCH$_2$, S); 2H at 3.72 ppm (CH$_2$S→O, e.S.); 9H at 1.44 ppm

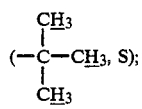

9H at 1.35 ppm

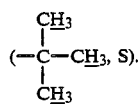

(b)
7-[2-(2-tritylamino-4-thiazolyl)-2-t-butoxycarbonylmethoxyiminoacetamido]-3-[(3-hydroxy-1,2,4-triazin-5-yl)-thiomethyl]-3-cephem-4-t-butylcarboxylate 1-S-oxide, syn isomer

Agitate a solution of 0.8 g of the brominated derivative from Example 2a for 2 hours at room temperature along with 0.16 g 3-hydroxy 5-mercapto 1,2,4-triazine in dimethylformamide.

The solvent is vacuum-evaporated and the residue dissolved in isopropyl ether. The precipitate is dried by vacuum filtration and is dissolved in the minimum necessary quantity of methylene chloride. Chromatography is carried out on silica gel (50 g).

Eluting with ethyl acetate, 0.57 g of the expected product is obtained.

(c) CM 40 515

Proceed with 0.2 g of the product described above, as indicated in Example 1c.

0.15 g CM 40 515 is obtained.

NMR Spectrum 1H at 8.75 ppm (NH CO, D, J=8.5 Hz); 1H at 7.97 ppm (H triazine, S); 1H at 6.93 ppm (H thiazole, S); 5H at 6.50 ppm (H exchanges e.S.); 1H at 5.95 ppm (H$_7$, D-D, J$_1$=8.5 Hz, J$_2$=4.5 Hz); 1H at 4.95 ppm (H$_6$, D, J=4.5 Hz); 2H at 4.59 ppm (OCH$_2$, S); 1H at 4.40 ppm (CH S-triazine, A of AB, J$_{AB}$=15 Hz); 1H at 4.0 ppm (CH S-triazine, B of AB, J$_{AB}$=15 Hz); 2H at 3.75 ppm (CH$_2$S→O, e.S.).

EXAMPLE 3

7-[2-(2-amino-4-thiazolyl)-2-(2-carboxy-2-propyloxyimino)acetamido]-3-[(3-hydroxy-1,2,4-triazin-5-yl)thiomethyl]-3-cephem-4-carboxylic acid 1-S-oxide, syn isomer (CM 40 421)

(a)
7-[2-(2-tritylamino-4-thiazolyl)-2-(2-t-butoxycarbonyl-2-propyloxyimino)acetamido]-3-bromomethyl-3-cephem-4-t-butylcarboxylate 1-S-oxide, syn isomer

To a solution of 5 g 7-amino 5-bromomethyl 3-cephem 4-t-butyl carboxylate 1-S-oxide hydrochloride in 90 ml methylene chloride, add 1.72 ml triethylamine, 7.57 g 2-(2-tritylamino-4-thiazolyl)-2-(2-t-butoxycarbonyl-2-propyloxyimino)acetic acid, 2.84 g dicyclohexylcarbodiimide and 0.1 g hydroxybenzo triazole. Agitate the mixture for 15 hours at room temperature, then filter out the dicyclohexylurea formed.

After evaporation of the solvent, carry out column chromatography of the residue on silica gel (250 g). Upon eluting with hexane/ethyl acetate 50/50 (vol/vol) 4.3 g of the expected product is obtained.

NMR Spectrum (in deutero-dimethylsulfoxide solution)

1H at 8.70 ppm (NH-Trit, S); 1H at 8.07 ppm (NH—CO, D, J=9 Hz); 15H at 7.25 ppm (H Trit, S); 1H at 6.72 ppm (H thiazole, S); 1H at 5.88 ppm (H$_7$ D-D, J$_1$=9 Hz, J$_2$=4 Hz); 1H at 4.96 ppm (H$_6$, D, J=4 Hz); 2H at 4.50 ppm (CH$_2$Br, AB, J$_{AB}$=12 Hz); 2H at 3.77 ppm (CH$_2$ in 2, e.S.); 9H at 1.45 ppm

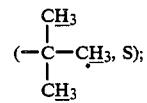

6H at 1.37 ppm

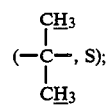

9H at 1.27 ppm

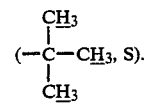

(b)
7-[2-(2-tritylamino-4-thiazolyl)-2-(2-t-butoxycarbonyl-2-propyloxyimino)acetamido]-3-[(3-hydroxy-1,2,4 triazin-5-yl)thiomethyl]-3-cephem-4-t-butylcarboxylate 1-S-oxide, syn isomer

To a solution of 1 g of the product obtained previously in 12 ml dimethylformamide, and 0.18 g 3-hydroxy 5-mercapto 1,2,4 triazine. Add 0.15 ml triethylamine. Agitate for 3 hours at room temperature, then precipitate the expected product by addition of isopropyl ether.

(c) CM 40 421

Agitate a solution of 0.89 g of the compound obtained above in 9 ml trifluoroacetic acid for 30 minutes at room temperature. Concentrate the solution under vacuum until a volume of 5 ml is obtained, and add isopropyl ether until precipitation. Dry the precipitate by vacuum filtration and dissolve in 800 ml acetone/ethanol 50/50 (vol/vol). Concentrate under vacuum until a volume of 50 ml is reached then separate the precipitate by filtration.

NMR Spectrum (in deutero-dimethylsulfoxide solution)

1H at 8.35 ppm (NHCO, D, J=9 Hz); 1H at 7.95 ppm (H$_6$ triazine, S); 5H at 7.30 ppm (2CO$_2$H, NH$_2$, OH, e.S.); 1H at 6.85 ppm (H thiazole, S); 1H at 5.96 ppm (D-D, $J_1=9$ Hz, $J_2=4$ Hz); 1H at 4.95 ppm (H$_6$, D, J=4 Hz); 2H at 4.20 ppm (C$\underline{H}_2$S, AB, $J_{AB}=13$ Hz); 2H at 3.75 ppm (C$\underline{H}_2$ in 2, e.S.); 6H at 1.43 ppm (C$\underline{H}_3$, S).

EXAMPLE 4

7-[2-(2-amino-4-thiazolyl)-2-(1-carboxy-2-cyclobutyloxyimino)acetamido]-3-[(3-hydroxy-1,2,4-triazin-5-yl)thiomethyl]-3-cephem-4-carboxylic acid 1-S-oxide, syn isomer. (CM 40 732)

(a)

7-[2-(2-tritylamino-4-thiazolyl)-2-(1-t-butoxycarbonyl-1-cyclobutyloxyimino)acetamido]-3-bromomethyl-3-cephem-4-t-butylcarboxylate 1-S-oxide, syn isomer To a solution of 4.4 g 1-amino 3-bromomethyl 3 cephem 4-t-butyl carboxylate 1-S-oxide hydrochloride in 70 ml anhydrous methylene chloride, add 1.5 ml triethylamine, 5.1 g 2-(2-tritylamino 4-thiazolyl)acetic acid, cis-isomer, 2.4 g dicyclohexylcarbodiimide and 0.1 g 1-hydroxy benzotriazole. Agitate for 1 hour at room temperature, then filter off the dicyclohexylurea formed and concentrate the solution to 20 ml under vacuum. Carry out chromatography on a silica gel column (150 g). Elution with hexane/ethyl acetate 40/60 (vol/vol) yields, after evaporation of the solvent 4.8 g of the expected product.

NMR Spectrum 1H at 7.90 ppm (NHCO, D, J=9 Hz); 15H at 7.26 ppm (Aromatic H, S); 1H at 6.97 ppm (N$\underline{H}$-trityl, e.S.); 1H at 6.65 ppm (H thiazole, S); 1H at 6.18 ppm (H$_7$, D-D, $J_1=9$ Hz, $J_2=4.5$ Hz); 2H at 3.4 ppm (C$\underline{H}_2$S→O, e.S); 6H between 1.5 and 2.6 ppm (cyclobutyl, M); 9H at 1.46 ppm

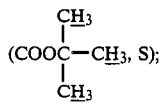

9H at 1.36 ppm

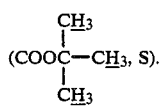

(b) and (c)

From the derivative produced above, and proceeding as in Example 3b using 3-hydroxy 5-mercapto 1,2,4-triazine and after liberating the amine and acid functions as in Example 3c, the expected product is obtained.

NMR Spectrum 1H at 13 ppm (e.S., O$\underline{H}$); 5H between 8 and 10 ppm (M, CON$\underline{H}$, COOH, N$\underline{H}_2$); H at 7.95 ppm (S, H triazine); 1H at 6.83 ppm (S, H triazole); 1H at 6.00 ppm (M, H$_7$); 1H at 4.97 ppm (M, H$_6$); 1H at 4.40 ppm (A of AB, $J_{AB}=13$ Hz, CH$_2$S); 1H at 4.00 ppm (B of AB, $J_{AB}=13$ Hz, CH$_2$); 2H at 3.97 ppm (M, C$\underline{H}_2$→O); H between 1.5 and 2.5 ppm (M, □ ).

EXAMPLE 5

7-[2-(2-amino-4-thiazolyl)-2-(1-carboxyl-1-cyclopentyloxyimino)acetamido]-3-[(3-hydroxy-1,2,4-triazin-5-yl)thiomethyl]-3-cephem-4-carboxylic acid 1-S-oxide, syn isomer.

(a)

7-[2-(2-tritylamino-4-thiazolyl)-2-(1-t-butoxycarbonyl-1-cyclopentyloxyimino)acetamido]-3-bromomethyl-3-cephem-4-t-butyl carboxylate 1-S-oxide, syn isomer Proceed as in Example 4a using 2-(2-tritylamino 4-thiazolyl) 2-(1-t-butoxycarbonyl 1-cyclopentyl oxyimino)acetic acid, cis isomer.

NMR Spectrum 1H at 7.83 ppm (NHCO, D, J=9 Hz); 15H at 7.27 ppm (aromatic H, S); 1H at 6.93 ppm (N$\underline{H}$-trityl, e.S.); 1H at 6.14 ppm (H$_6$, D-D, $J_1=9$ Hz, $J_2=\overline{4, 5}$ Hz); 2H at 3.5 ppm (CH$_2$S→O, AB, $J_{AB}=17$ Hz); 8H between 1.3 and 2.3 ppm (cyclopentyl, M); 9H at 1.50 ppm

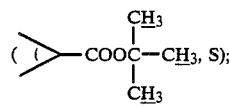

9H at 1.35 ppm

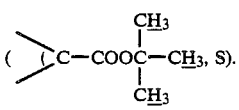

(b) and (c)

Starting with the above mentioned brominated derivative and proceeding as in Example 3b with 3-hydroxy 5-mercapto 1,2,4-triazine and after liberation of the amine and acid functions as in Example 3c, the expected product is obtained.

EXAMPLES 6 to 8

Proceeding as in Examples 1, 3 and 4, starting with the brominated derivatives described in Examples 1a, 3a and 4a, but replacing 3-hydroxy 5-mercapto 1,2,4-triazine with an equivalent quantity of 5-hydroxy 3-mercapto 1,2,4-triazine, after liberation from the protective groups, the following compounds result:

7-[2-(2-amino-4-thiazolyl)-2-methoxyiminoacetamido]-3-[(5-hydroxy-1,2,4-triazin-3-yl)thiomethyl]-3-cephem-4-carboxylic acid 1-S-oxide, cis isomer. (CM 40 970)

7-[2-(2-amino-4-thiazolyl)-2-(2-carboxy-2-propyloxyimino)acetamido]-3-[(5-hydroxy-1,2,4-triazin-3-yl)thiomethyl]-3-cephem-4-carboxylic acid 1-S-oxide, cis isomer. (CM 40 766)

7-[2-(2-amino-4-thiazolyl)-2-(1-carboxy-1-cyclobutyloxyimino)acetamido]-3-[(5-hydroxy-1,2,4-triazin-3-yl)thiomethyl]-3-cephem-4-carboxylic acid 1-S-oxide, cis isomer. (CM 40 881)

Their NMR Spectra are indicated in the following table.

| Example | Compound | NMR Spectrum |
|---|---|---|
| 6 | CM 40 970 | 1 H at 8.90 ppm (D, J = 9 Hz, CON$\underline{H}$); |

| Example | Compound | NMR Spectrum |
|---|---|---|
| | | -continued |
| | | 1 H at 7.60 ppm (S, H triazine);<br>1 H at 6.86 ppm (S, H thiazole);<br>4 H at 5.20 and 7.20 ppm (e, S., NH$_2$, OH, COOH);<br>1 H at 5.87 ppm (D of D, J$_1$ = 9 Hz, J$_2$ = 4 Hz, H$_7$),<br>1 H at 4.92 ppm (D, J = 4 Hz, H$_6$);<br>1 H at 4.33 ppm (A of AB, J$_{AB}$ = 13 Hz, CH$_2$S);<br>1 H at 4.05 ppm (B of AB, J$_{AB}$ = 13 Hz, CH$_2$S);<br>5 H at 3.84 ppm (e, S.,<br><br>CH$_3$ON, CH$_2$S→O) |
| 7 | CM 40 766 | 5 H between 8.5 and 11 ppm (e, S., NH$_2$, OH, COOH);<br>1 H at 8.45 ppm (D, J = 9 Hz, CONH);<br>1 H at 7.62 ppm (S, H triazine);<br>1 H at 6.89 ppm (S, H thiazole);<br>1 H at 6.00 ppm (D of D, J$_1$ = 9 Hz, J$_2$ = 4 Hz, H$_7$);<br>1 H at 4.95 ppm (D, J = 4 Hz, H$_6$);<br>1 H at 4.40 ppm (A of AB, J$_{AB}$ = 13 Hz, CH$_2$S);<br>1 H at 4.05 ppm (B of AB, J$_{AB}$ = 13 Hz, CH$_2$S);<br><br>2 H at 3.80 ppm (e, S., CH$_2$S→O);<br><br>6 H at 1.46 ppm (S, —C(CH$_3$)(CH$_3$)) |
| 8 | CM 40 881 | 1 H at 8.70 ppm (D, J = 9 Hz, NHCO);<br>4 H at 8.3 ppm (S. e., 2 COOH, NH$_2$);<br>1 H at 7.63 ppm (S, H trazine);<br>1 H at 6.89 ppm (S, H thiazole);<br>1 H at 6.0 ppm (D of D, J$_1$ = 9 Hz, J$_2$ = 4 Hz, H$_7$);<br>1 H at 5.0 ppm (D, J = 4 Hz, H$_6$);<br>1 H at 4.40 ppm (A of AB, J$_{AB}$ = 12 Hz, CH$_2$S);<br>1 H at 4.10 ppm (B of AB, J$_{AB}$ = 12 Hz, CH$_2$S)<br><br>2 H at 3.80 ppm (M, CH$_2$S→O);<br><br>6 H between 1.5 2.5 ppm (M, ▢) |

We claim:

1. A cephalosporin derivative having the formula

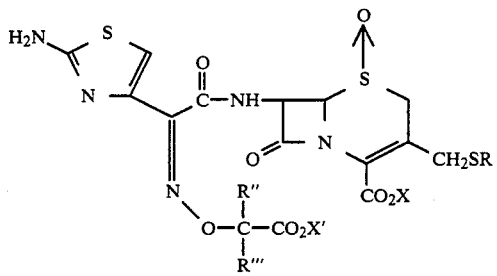

wherein the sulfoxide function is in the (S) stereoisomeric form;

R is selected from the group consisting of

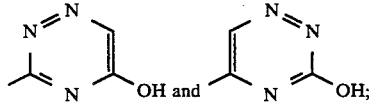

R" and R'" each separately represents hydrogen or alkyl of from one to three carbons, or, R" and R'" taken together with the carbon to which they are attached constitute a cyclobutyl or cyclopentyl ring; and X and X' are separately selected from the group consisting of hydrogen;

alkali metal cations;

alkaline earth cations;

cations resulting from protonation of a compound selected from the group consisting of ethylenediamine, triethanolamine, diethanolamine, ethanolamine, and tromethamine;

tertiary butyl;

organic radicals selected from the group consisting of phthalidyl, pivaloyl oxymethyl, acetoxymethyl, ethoxycarbonyl-oxymethyl, 1-(ethoxy carbonyloxy)ethyl, acetonyl, alpha-methoxy-alpha-carbomethoxy methyl, carbomethoxymethyl, and carbethoxymethyl;

or a pharmaceutically-acceptble acid addition salt of the compound in which X is H, tertiary butyl, or said organic radical.

2. An antibacterial pharmaceutical composition comprising an antibacterially effective amount of at least one cephalosporin of claim 1 plus a pharmaceutically-acceptable carrier.

3. An antibacterially-effective pharmaceutical composition of claim 2 in dosage form, wherein the cephalosporin constitutes 10–10,000 mg/dose.

4. A method for treating bacterial infections comprising administering one to four doses per day of an antibacterial pharmaceutical composition of claim 3.

* * * * *